United States Patent
Kindlein et al.

(10) Patent No.: US 7,288,061 B2
(45) Date of Patent: Oct. 30, 2007

(54) DEVICE FOR IMPLANTING A ROW OF RADIOACTIVE SEEDS AND NON-RADIOACTIVE SPACERS IN AN ANIMAL BODY

(75) Inventors: Johann Kindlein, Oberhausen (DE); Arie Luite Visscher, Driebergen (NL); Ulrike Lutz, Arnhem (NL); Jeroen Schuurman, Amersfoort (NL); Mark Alexander Adam, Amsterdam (NL)

(73) Assignee: Nucletron B.V., Veenendaal (NL)

( * ) Notice: Subject to any disclaimer, the term of this patent is extended or adjusted under 35 U.S.C. 154(b) by 646 days.

(21) Appl. No.: 10/674,356

(22) Filed: Oct. 1, 2003

(65) Prior Publication Data
US 2005/0177020 A1 Aug. 11, 2005

(30) Foreign Application Priority Data
Oct. 7, 2002 (EP) ............................ 02079170

(51) Int. Cl.
*A61N 5/00* (2006.01)
(52) U.S. Cl. .......................................... 600/3
(58) Field of Classification Search ............ 600/1–8, 600/431, 433–435; 604/48, 57–63, 93.01, 604/117, 264, 265, 272, 890.1, 891.1
See application file for complete search history.

(56) References Cited

U.S. PATENT DOCUMENTS

| | | | |
|---|---|---|---|
| 5,092,834 A * | 3/1992 | Bradshaw et al. ............ | 600/7 |
| 5,928,130 A | 7/1999 | Schmidt | |
| 5,976,067 A * | 11/1999 | Tucker et al. ................. | 600/2 |
| 6,095,967 A | 8/2000 | Black et al. | |
| 6,210,315 B1 | 4/2001 | Andrews et al. | |
| 6,450,937 B1 | 9/2002 | Mercereau et al. | |
| 2003/0092958 A1* | 5/2003 | Terwilliger et al. ........... | 600/8 |
| 2003/0109769 A1* | 6/2003 | Lowery et al. ................ | 600/7 |

FOREIGN PATENT DOCUMENTS

| | | |
|---|---|---|
| EP | 1 070 519 A1 | 1/2001 |
| WO | WO97/25102 A1 | 7/1997 |
| WO | WO 01/30434 A1 | 5/2001 |
| WO | WO 02/20089 A1 | 3/2002 |

* cited by examiner

*Primary Examiner*—John P. Lacyk
(74) *Attorney, Agent, or Firm*—Birch, Stewart, Kolasch & Birch, LLP

(57) ABSTRACT

A device for implanting radioactive seeds and non-radioactive spacers in a desired configuration in an animal body for effecting radiation therapy. An elongated hollow needle is inserted in the body. A pushing element implants the row of seeds and spacers though the hollow needle towards the desired location. A tube shaped element receives the row of seeds and spacers. A lube shaped sleeve having open ends is used to insert the tube shaped element through the needle and toward the location. The pushing elements pushes the row of seeds and spacers into the desired location while still being carried in the tube shaped element.

18 Claims, 5 Drawing Sheets

DEVICE FOR IMPLANTING A ROW OF RADIOACTIVE SEEDS AND NON-RADIOACTIVE SPACERS IN AN ANIMAL BODY

This nonprovisional application claims priority under 35 U.S.C. § 119(a) on patent application Ser. No(s). 02079170.3 filed in EUROPE on Oct. 7, 2002, which is (are) herein incorporated by reference.

BACKGROUND OF THE INVENTION

1. Field of the Invention

The invention relates to a device for implanting at least one row of X radioactive seeds and Y non-radioactive spacers with $X \in [1, 2, \ldots]$ and $Y \in [0, 1, \ldots]$ in a desired configuration to a desired location in an animal body for effecting radiation therapy of cancerous tissue in said body, said device comprising: at least one elongated hollow needle with an open distal end to be inserted towards said desired location in the body and with a proximal end to be connected to a seed loading apparatus; and at least one pushing element for implanting during retraction of the elongated hollow needle said row of radioactive seeds and non-radioactive spacers from said seed loading apparatus through said hollow needle towards said location.

The invention moreover relates to a seed loading apparatus provided with an implanting device according to the invention as well as to a row of X radioactive seeds and Y non-radioactive spacers with $X \in [1, 2, \ldots]$ and $Y \in [0, 1, \ldots]$ in a desired configuration, wherein said seeds and spacers are accommodated in a tube-shaped element according to the invention.

2. Description of the Background

In the European patent application no. 1070519 in the name of the applicant of this application an apparatus for implanting radioactive seeds in e.g. the male prostate gland is disclosed. Under ultrasound guidance using an ultrasound probe and using a first template implant needles, hereinafter needles, are placed in the prostate gland. Under fluoroscopy the positions of the needles are checked and for every individual needle the length and configuration of the row or train of seeds/spacers is determined using a radiation therapy treatment module.

In order to finalize the implant procedure each row of seeds/spaces is urged through it's corresponding needle towards the open distal end of the hollow needle in the prostate gland using a pushing element. Subsequently the pushing element is fixed and the hollow needle is retracted over a distance equal or slightly greater than the length of the row of seeds/spacers, thereby introducing the row of seeds/spacers at it's intended postion within the prostate gland.

Next the pushing element is withdrawn into the seed loading unit for pushing a next seed-spacer row through another needle into the prostate gland. The delivery of subsequent seed/spacers rows in the prostate gland continues until each needle has been retracted and a number of seed-spacer rows equal to the number of needles has been positioned at different locations within in the prostate gland.

The known apparatus is then disconnected and the needles are retracted from the patient completely. A final control/check of the geometry/presence of the implanted seeds in the prostate gland is performed under fluoroscopy or another imaging technique and after removal of the ultrasound probe the patient is hospitalized for recovery.

Examples of configurations of a row of radioactive seeds and non-radioactive spacers are for example disclosed in the International Patent Application Nos. WO02/20089, WO00/09211, WO99/59675 and in the U.S. Pat. No. 4,815,449.

Each row of radioactive seeds and non-radioactive spacers as disclosed in the above prior art patent publications has the disadvantage that after insertion into the body or near to the tissue to be irradiated the inserted seeds and spacers are only accommodated/enveloped by tissue of the body.

Furthermore all rows of seeds/spacers as disclosed in the cited prior art patent publications can only be configured in a seeds/spacer configuration consisting of a repeated configuration "seed, spacer, seed, spacer, . . . ". This gives less flexibility in configuring the treatment plan and seed/spacer trains in another configuration/sequence.

That may have a consequence that upon movements of the body in which the row of radioactive seeds and non-radioactive spacers has been inserted the radioactive seeds and non-radioactive spacers may move through the body/the tissue to be irradiated and as a consequence of these movements undesired irradiation of other tissue will occur.

This will be disadvantageous for the therapeutic treatment since the distribution of the radioactive seeds and non-radioactive spacers in each row has been calculated with great accuracy in order to reach an optimal result in respect of the irradiation of the tissue to be treated. In general not one but a number or even a great number of rows of radioactive seeds and non-radioactive spacers, each arranged with a predetermined pitch, is inserted in order to irradiate the tissue, often cancerous tissue and their exact position within the tissue has been calculated using a specific radiation therapy treatment module in order to spare/avoid undesired radiation of fragile tissue or organs, e.g. the urethra, bladder or rectum during the treatment of the prostate gland.

There is therefore a need for rows of radioactive seeds and non-radioactive spacers for brachytherapeutic treatment of tissue with radioactive radiation in which mutual displacement of the seeds/spacers after insertion of the row into the body is avoided due to e.g. movements of the patient or other disturbances within the body like swellings, blood circulation etc.

SUMMARY OF THE INVENTION

The present invention aims to provide a tool and method for implanting rows of radioactive seeds and spacers without having the above described prior art drawbacks and without modifying the existing implantation techniques.

According to the inventing the device further comprises at least one tube-shaped element with at least one open end to be inserted through said hollow needle towards said desired location; and at least one tube-shaped sleeve member with an open distal and open proximal end for inserting said tube-shaped element through said hollow needle towards said desired location, wherein said tube-shaped element serves to accommodate said row of radioactive seeds and non-radioactive spacers.

With the use of a tube-shaped element which serves to accommodate said row of radioactive seeds and non-radioactive spacers it is avoided that the row of seeds/spacers displaces within the organ to be treated after insertion due to e.g. movements of the patient or other disturbances within the body like swellings, blood circulation etc. The proposed radiation therapy treatment is not adversely affected and undesired irradiation of other tissue, for example fragile organs like the urethra, the bladder or the rectum is avoided.

Preferably said tube-shaped element is inserted through said hollow needle prior to the insertion of the row of radioactive seeds and non-radioactive spacers.

More in particular said pushing element is constructed as a rigid pushing rod, whereas in another embodiment the pushing element is constructed as a drive wire of the seed loading apparatus.

In order to avoid the insertion of said tube-shaped sleeve member past the proximal end within the elongated hollow needle said tube-shaped sleeve member is provided at his proximal end with a stopper element, which stopper element in a specific embodiment is constructed as a disk shaped end plate.

For a proper functioning of the implanting device according to the invention are the outer dimensions of the tube-shaped sleeve member and the tube-shaped element equal or slightly smaller than the inner dimensions of said hollow needle and furthermore are the inner dimensions of the tube-shaped sleeve and the tube-shaped element equal or slightly larger than the outer dimensions of said radioactive seed and non-radioactive spacer.

Furthermore, for a proper functioning of the implanting device when implanting a row of seeds/spacers into the animal body the dimensions of the several parts of the implanting device conforms the equation $$l \geq (X+Y)s \text{ and } S \leq (L-l),$$

in which
l is the length of the tube-shaped element;
s is the length of one individual seed/spacer;
L is the length of the hollow needle;
S is the length of the tube-shaped sleeve member.

This makes it possible to use tube-shaped elements specifically designed for a row of seeds/spacers of a specific length, and thus avoiding the above-described problems of the prior art rows, namely the displacement of the seeds and spacers.

According to a specific embodiment said tube-shaped element is made of a bio-absorbable material, and more in particular at least the proximal end of said tube-shaped element is collapsible. This last feature creates a tube-shaped element completely enclosing the row of seeds/spacers inside the body after retraction of the hollow needle and further avoids a possible displacement of the seeds/spacers in the organ to be irradiated.

Moreover the tube-shaped element may have two open ends or one closed end, more in particular a closed distal end.

In another embodiment the tube-shaped element has a oval-shaped cross-section prior to the insertion through the hollow needle, and wherein the tube-shaped element has a circular cross section when inserted in the hollow needle.

However also tube-shaped elements having a circular cross section are very suitable for use with the implanting device according to the invention.

More especially the tube-shaped element according to the invention is made of a flexible or elastic material capable for exerting an inwardly directed force on the row of radioactive seeds and non-radioactive spacers.

These two features (oval shape and flexible/elastic) creates an improved fixation of the row of seeds/spacers within the tube-shaped element and the animal body further limiting the risk of displacement of the seeds/spacers through the animal body.

This fixation phenomenon can be further improved, as according to the invention at least the open proximal end of said tube-shaped element is collapsable.

BRIEF DESCRIPTION OF THE DRAWINGS

The invention will now be described in more detail with reference to the accompanying drawings, which show.

DETAILED DESCRIPTION OF THE PREFERRED EMBODIMENTS

It is to be noted that the following description will be made with respect to treatment of a prostate gland. However, the invention may be used in far more applications in which (radioactive) seeds are deposited manually or with the use of a seed loading apparatus in other parts of an animal body.

Figure 1:
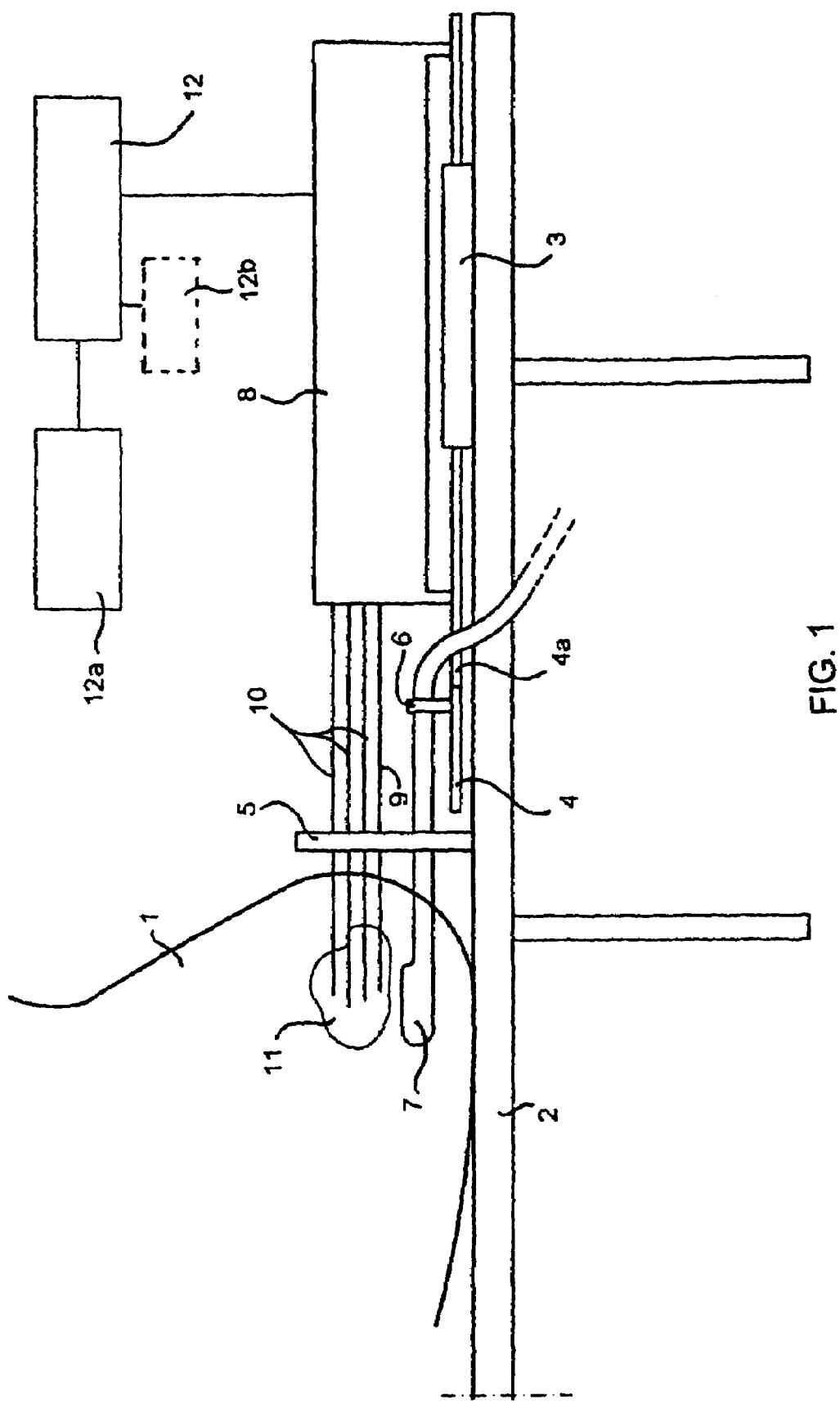
FIG. 1 a schematic view of an apparatus for implanting radioactive seeds using a hollow needle according to the state of the art.

FIG. 1 shows in very schematic form various elements of a device for implanting radioactive seeds into a prostate gland. A patient 1 is shown lying in lithotomy position on a table 2. Fixedly connected to the table 2 is a stepper unit 3. Stepper unit 3 comprises a drive to move movable tables 4 and 4a stepwise. Connectable to table 4 is a template 5. By means of a holder 6 a transrectal ultrasound probe 7 is fixedly connectable to table 4a. A needle 9 is used for fixing the prostate gland 11 in position relative to the template 5.

A number of needles 10 is fixed into position through the template 5 in the prostate gland 11. The template 5 determines the relative positions of the needles 10 in two dimensions. The needles 10 are open at their distal ends and are sealed of by a plug of biocompatible, preferably bio-absorbable wax. In a first embodiment the seed loading unit 8 is connectable to the table 4. In a second embodiment the seed loading unit 8 is a stand alone unit.

A well-known therapy planning module 12a is provided for determining the number and relative positions of seeds in each needle for implantation in the prostate gland 11. Such therapy planning module 12a usually comprises a computer programmed with a therapy planning program. One such a therapy planning program is marketed under the trademarks PLATO™, SPOT™ and SPOT PRO™ by Nucletron B.V. of the Netherlands. Other such programs are also known. The therapy planning module 12a is connected to the seed loading unit 8 through a control device 12 for controlling the number of seeds for each needle. The control device 12 may be a separate device or may be an integrated part either of the seed loading unit 8 or of the therapy planning module 12a or may be embodied in the software of the therapy planning module 12a or of the seed loading unit 8.

The device shown in FIG. 1 operates as follows. A patient 1 is under spinal or general anesthesia and lying on the operating table 2 in lithotomy position. The transrectal ultrasound probe 7 is introduced into the rectum and the probe is connected to the stepper unit 3 and table 4 through holder 6. On an image screen, well known, an image may be seen of the inside of the patient in particular of the prostate gland 11 as seen from the point of view of the ultrasound probe 7.

The template 5 is attached to the stepper unit 3. Thereby the correlation of the ultrasound image geometry and the template 5 is guaranteed. The prostate gland 11 is fixed relative to the template and the stepper unit 3 and the ultrasound probe by means of one or more needles 10. Subsequently further needles 10 are introduced in the body and the prostate gland under ultrasound guidance one by one.

Moving the ultrasound probe with the stepper unit 3 longitudinally within the rectum controls the needle depths. After all needles 10 have been placed their positions relative to the prostate gland 11 are determined in at least one of several known ways. In a known way the therapy planning module 12a determines how the needles 10 are to be placed in the prostate and how many radioactive seeds are to be placed in what order in each of the needles 10. The information about the desired placement of the radioactive seeds in the needles 10 is used to control the seed loading unit 8.

Usually the radioactive seeds are spaced from each other by non-radioactive spacers. For example seeds of 1 cm length may be spaced by spacers also of 1 cm length. Other measures of seeds and spacers are imaginable. A row of seeds and spacers loaded or to be loaded into a needle will be called a seed train or a train of seeds or a seed-spacer train. For each needle 10 the configuration of an applicable seed-spacer train is determined by the therapy planning module 12a. The seed loading unit 8 is controlled by the control device 12 to make up a seed-spacer train for each needle 10.

The creation of a specific seed-spacer train will not be described herein, but is for example disclosed in the European patent application no. 1 070 519 in the name of the applicant of this application and herewith incorporated by reference. Once a seed-spacer train is to be or has been made up for a specific needle a connection is made to the specific needle. After the seed-spacer train has been made up it is urged into the specific needle by a pushing drive, that is part of the seed loading unit 8.

Since all elements of the seed loading unit 8 and the needles 10 and their interconnections are of specific preknown dimensions, which may or may not be the same for all like elements and such dimensions have been made known, e.g. pre-loaded in or pre-entered via a keyboard 12b to the control device 12 the pushing drive pushes with a pushing element, e.g. a pushing wire the seed-spacer train just until it reaches the distal end of the specific hollow needle. Subsequently the pushing wire is fixed in position and the specific needle is retracted over a distance equal to or slightly greater than the length of the seed-spacer train in it. Thereby the wax plug and the seed-spacer train are introduced in the prostate gland 11.

Next the pushing wire is withdrawn into the seed loading unit 8 for pushing a next seed-spacer train into the prostate gland 11. The delivery of seed-spacer trains in the prostate gland continues until each needle 10 has been retracted and a number of seed-spacer trains equal to the number of needles 10 has been delivered in the prostate gland 11. Subsequently the seed loading unit 8 is disconnected from the stepper unit 3 and the needles 10 are retracted from the patient completely. After the geometry of the implanted seeds has been checked under fluoroscopy or another method of checking the presence of the seeds in the prostate gland 11 and removal of the ultrasound probe 7 the patient 1 is hospitalized for recovery.

As stated above, each row of radioactive seeds and non-radioactive spacers as disclosed in the above prior art patent publications has the disadvantage that after insertion into the body or near to the tissue to be irradiated the inserted seeds and spacers are only accommodated/enveloped by tissue of the body.

Furthermore all rows of seeds/spacers as disclosed in the cited prior art patent publications can only be configured in a seeds/spacer configuration consisting of a repeated configuration "seed, spacer, seed, spacer, . . . ". This gives less flexibility in configuring the treatment plan and seed/spacer trains in another configuration/sequence.

Therefore, movements of the patient or blood circulation and swelling may result in a displacement of the radioactive seeds and non-radioactive spacers through the body thus adversely affecting the intended, conformal therapeutic radiation treatment as preplanned by the radiation therapy treatment module.

The displacement of the radioactive seeds and non-radioactive spacers within the body may result in an undesired irradiation of other tissue or fragile organs, whereas the original, intended treatment situation will no longer be met.

Figure 2A:
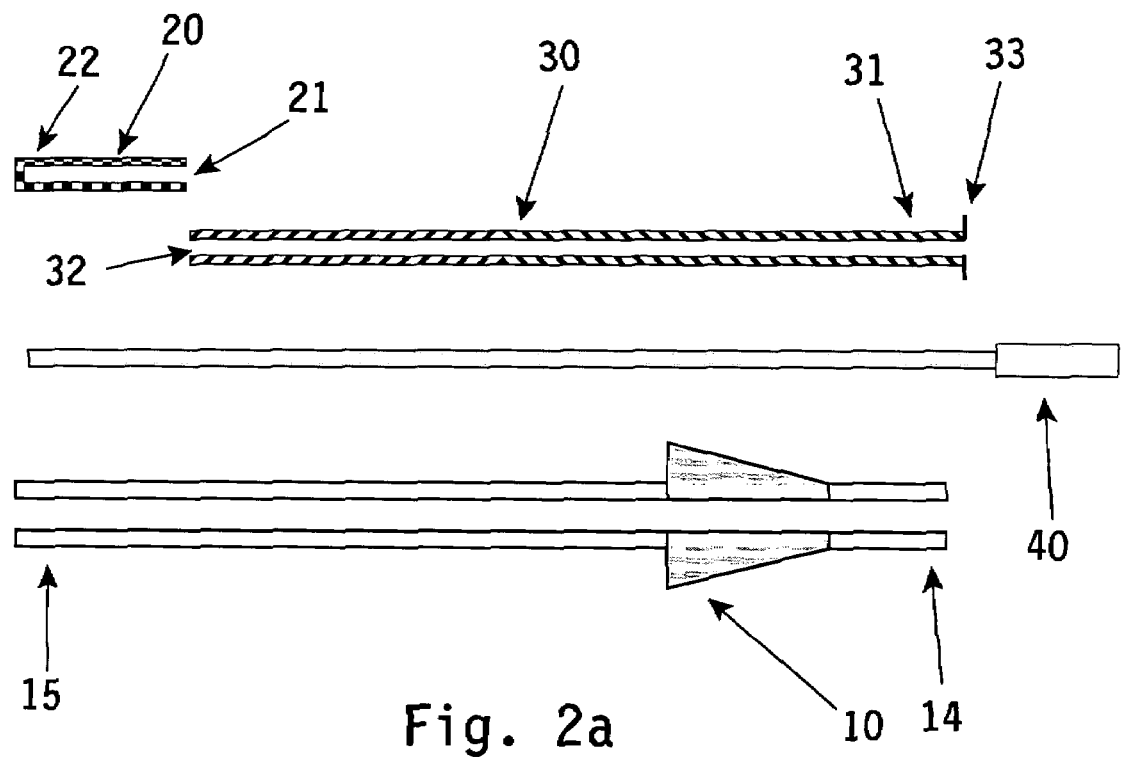
FIGS. 2a-2b a first embodiment of an implanting device according to the invention.
Figure 2B:
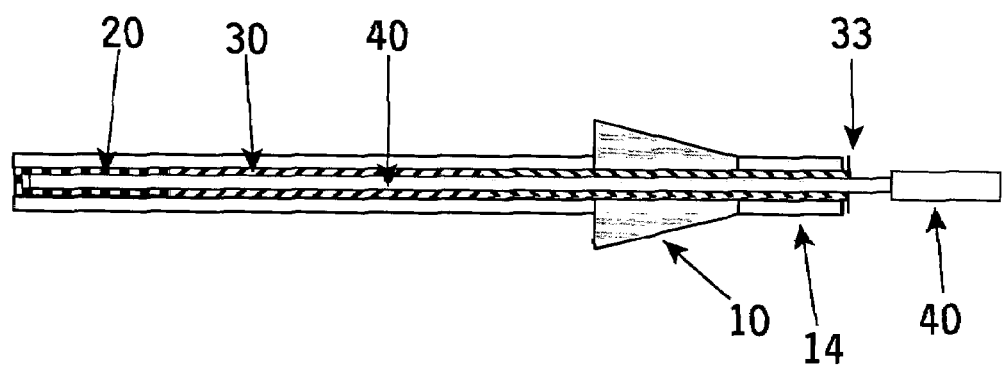

In FIG. 2a and FIG. 2b a first embodiment of an implanting device for a row of radioactive seeds and non-radioactive spacers is disclosed, which obviates the known prior art drawbacks without the necessity of modifying the existing implantation techniques.

Similar parts in the following Figures are denoted by the same reference numerals.

The implanting device according to the invention can be used as a replacement for the implant needle 10 as described in relation to FIG. 1.

The device 10 according of the invention comprises an elongated hollow needle 10 having a open distal end 15 to be inserted into the body near a desired location where irradiation of body tissue has to take place, as well as a proximal end 14. The open distal end 15 can be constructed as a sharp stylet, for an easy and correct insertion into the body. The implanting device further comprises a tube-shaped element 20 having a proximal end 21 and a distal end 22.

Said tube-shaped element 20 has at least one open end. In the embodiment shown in FIG. 2a the tube-shaped element 20 has a closed distal end 22 and an open proximal end 21, however another embodiments of the tube-shaped element 22 may consist of two open proximal and distal ends 21 respectively 22.

The device furthermore comprises a hollow tube-shaped sleeve member 30 with an open distal end 32 and an open proximal end 31.

The outer dimensions of both the tube-shaped element 20 and the tube-shaped sleeve member 30 are equal or slightly smaller than the inner dimensions of the elongated hollow needle 10, such that both the tube-shaped element 20 as well as the tube-shaped sleeve member 30 can be inserted in a slidable manner through the elongated hollow needle 10. In fact, the tube-shaped sleeve member 30 serves to insert the tube-shaped element 20 from the proximal end 14 through the hollow needle 10 towards the open distal end 15 of the hollow needle 10.

The implanting device 10 furthermore comprises a pushing rod 40 having at least the same length as the elongated hollow needle 10, which pushing rod is preferably made of a rigid material. The outer dimensions of the pushing rod 40 are equal or slightly smaller than the inner dimensions of the tube-shaped element 20 and tube-shaped sleeve member 30 respectively. Thus the pushing rod can be slidable inserted through the tube-shaped element and tube-shaped sleeve member.

FIG. 2b discloses the implanting device 10 with all separate parts mounted within the elongated hollow needle 10. The tube-shaped sleeve member 30 may be provided at its proximal end 31 with a stopper element 33, which stopper element 33 in this embodiment is constructed as a disk-shaped plate. The stopper element prevents the complete insertion of the sleeve member 30 inside said hollow needle 10, as the disk-shaped plate 33 abuts against the proximal end 14 of the elongated hollow needle 10.

FIGS. 3a-3f show the subsequent stages for implanting a row of radioactive seeds and non-radioactive spacers within the animal body towards a desired location and also elucidate the method for inserting such a row within an animal body.

In a first principle of the method for inserting a row of radioactive seeds and non-radioactive spacers within an animal body for radiation treatment of cancerous tissue, the assembly of the different parts of the implanting device 10 according to the invention as shown in FIG. 2b is inserted entirely into the animal body (here the male prostate gland 11) in the direction depicted by the arrow.

The tube-shaped element 20 as well as the tube-shaped sleeve member 30 and the pushing rot 40 are slidable received within the hollow elongated needle 10, which needle is inserted with its sharp open distal end 15 within the prostate gland 11.

Figure 3A:
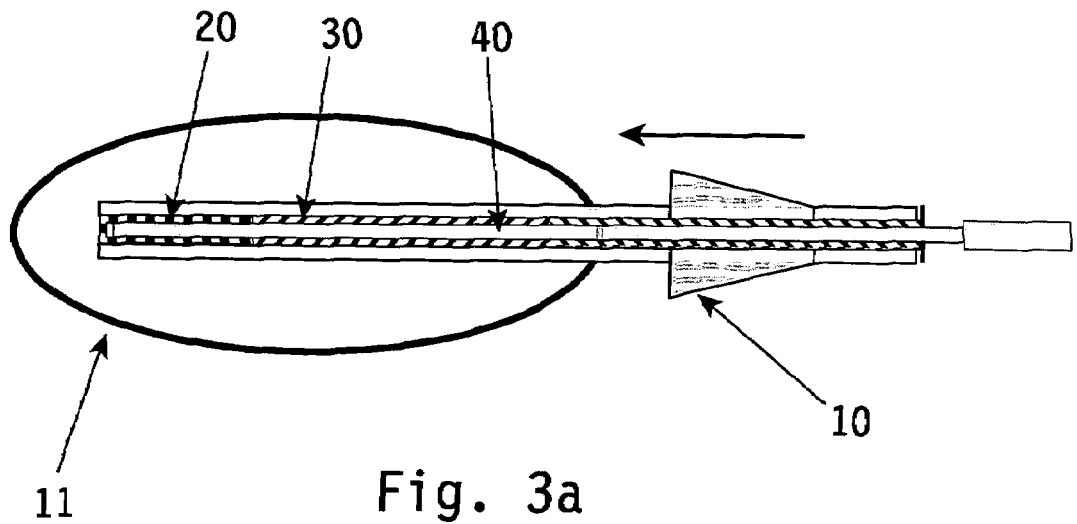
FIGS. 3a-3f subsequent stages showing the method for implanting a row of seeds/spacers using the implanting device according to the invention.
Figure 3B:
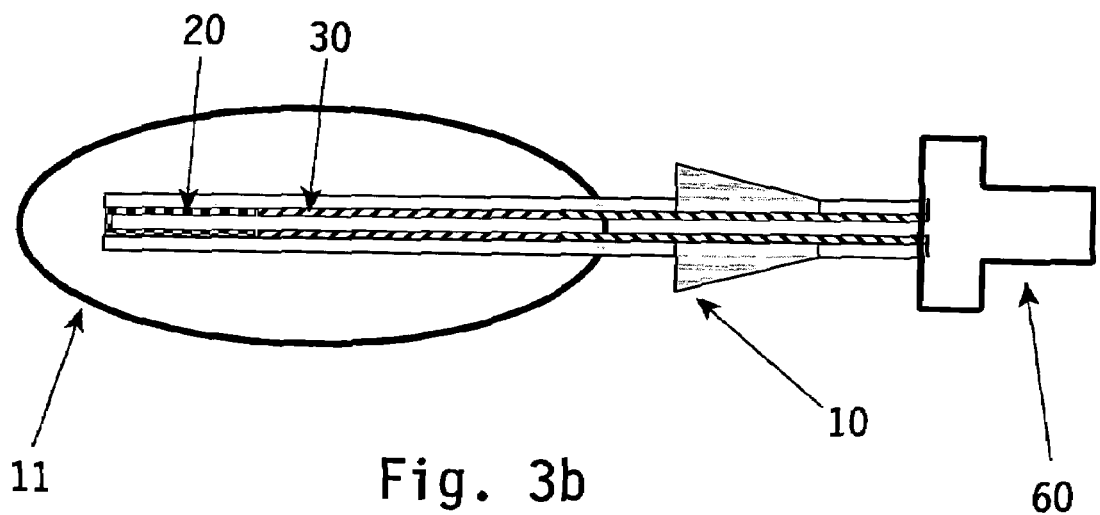
Figure 3C:
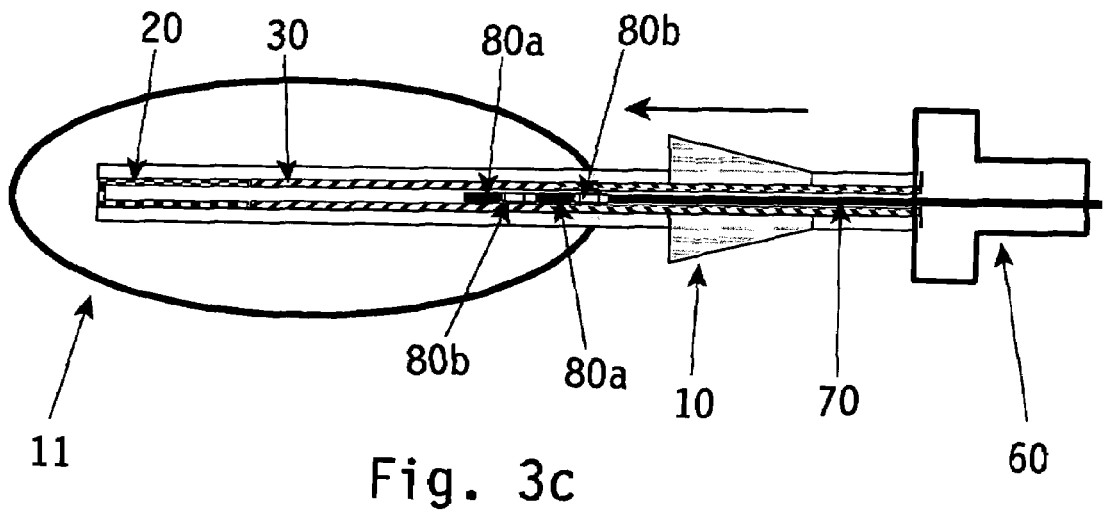
Figure 3D:
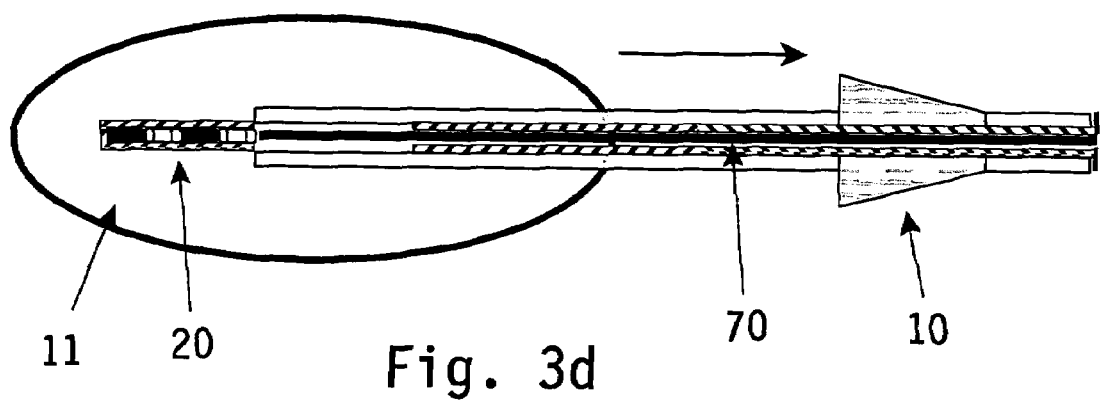

In FIG. 3b the pushing rod 40 is retracted from the hollow needle 10, whereas the proximal end 14 of the hollow needle 10 is connected to a seed loading apparatus. Such seed loading apparatus is for example described in conjunction with FIG. 1.

From the seed loading apparatus 60 a seed train consisting of radioactive seeds 80a and non-radioactive spacers 80b is inserted through the tube-shaped sleeve member 30 (and the hollow needle 10) towards the distal end 15 of the needle 10 (and the tube-shaped element 20) using a push wire 70 of the seed loading apparatus 60.

In an alternative insertion principle the seed train 80a-80b can be inserted through the hollow needle 10 manually using the pushing rod 40 as shown in FIG. 3a (and FIG. 2b).

Once the seed train 80a-80b is completely pushed toward the proximal end 15 of the hollow needle 10 and within the tube-shaped element 20 the push wire 70 is fixed and the hollow needle 10 together with the tube-shaped sleeve member 30 are retracted over a distance equal or slightly greater than the length of the tube-shaped element 20. As a result of this retraction of the hollow needle 10 and the tube-shaped sleeve member 30 the tube-shaped element 20 together with the seed train 80a-80b is introduced in the prostate gland 11. See FIG. 3e.

Subsequently the pushing wire 70 is retracted from the hollow needle 10 within the seed loading apparatus 60 for pushing a subsequent row of radioactive seeds and non-radioactive spacers through another needle 10 implanted in the prostate gland 11.

Once all rows of radioactive seeds and non-radioactive spacers are inserted into the prostate gland 11 through their corresponding implant devices 10 all hollow needles 10 including the tube-shaped sleeve members 30 are retracted from the patient. This situation is shown in FIG. 3e.

Now the row of radioactive seeds 80a and non-radioactive spacers 80b is accommodated within a tube-shaped element 20 their mutual relationship within the prostate gland 11 to be treated is not disturbed due to movements of the patient. Therefore, the risk of irradiation of fragile tissue or organs is herewith minimized or avoided. Moreover the conditions for the intended conformal radiation treatment are met and performed as preplanned.

Although the embodiment as disclosed in FIGS. 3a-3b comprises one closed distal end 22 and one open proximal end 21 in another embodiment the tube-shaped element 20 may comprise two open ends 21-22.

Figure 3E:
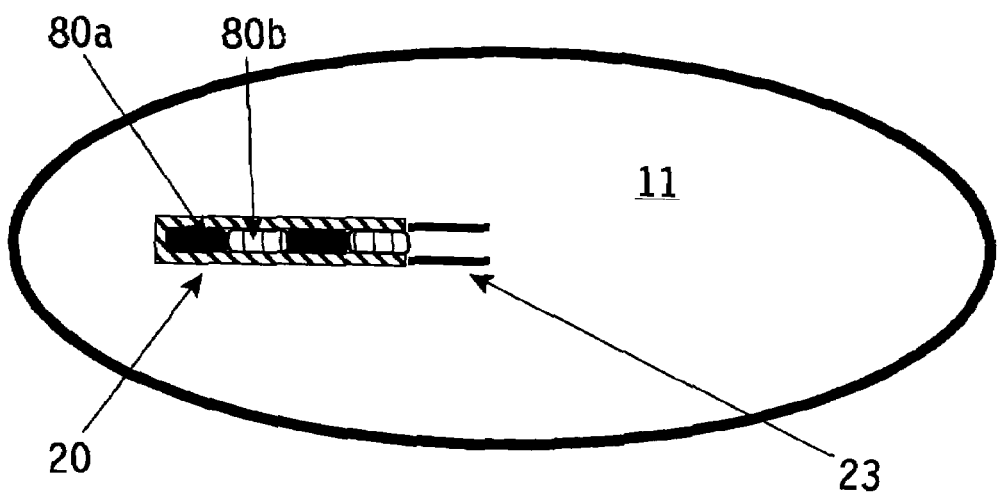
Figure 3F:
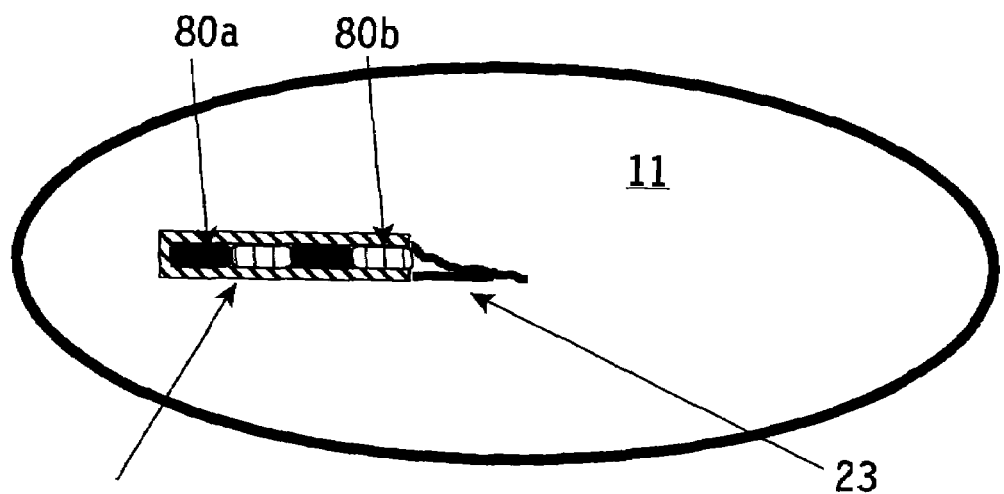

Preferably, the length of the tube-shaped element 20 is equal to the length of the seed train or the tube-shaped element 20 may be slightly longer than the corresponding seed train, as shown in FIG. 3e. Preferably radioactive seeds and non-radioactive having identical outer dimensions are used, and for each row of seeds/spacers having a specific configuration/length a tube-shaped element having a corresponding length can be used.

The tube-shaped element 20 can have a length slightly longer than the length of the seed/spacer train, wherein the part 23 of the proximal end 21 may have a smaller thickness than the rest of the tube-shaped element 20. This part 23 of the tube-shaped element 20 may collapse due to the tissue surrounding the tube-shaped element 20 after retraction of the hollow needle 10, creating a tube-shaped element 20 completely enclosing the seed train 80a-80b. This further avoids any possible displacement of the radio active seeds and non-radioactive spacers within tube-shaped element 20 (and prostate gland 11), thus preventing any undesired irradiation of other tissue or fragile organs such as the urethra, bladder or rectum.

The tube-shaped element 20 can be made from a bio-absorbable material.

In conjunction with the FIGS. 2a-2b and 3a-3f a tube-shaped element 20 has been described having a circular cross section of which the outer dimensions are equal or slightly smaller than the circular inner dimensions of the hollow needle 10.

Figure 4A:
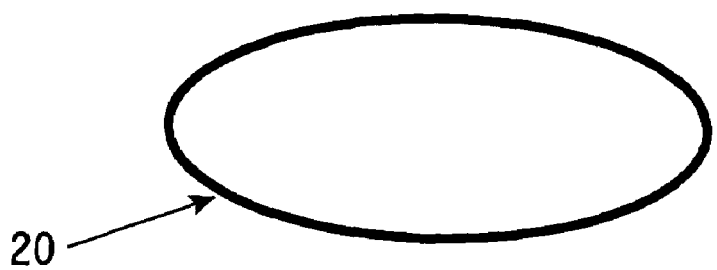
FIGS. 4a-4c another embodiment of a part of the implanting device according to the invention.
Figure 4B:
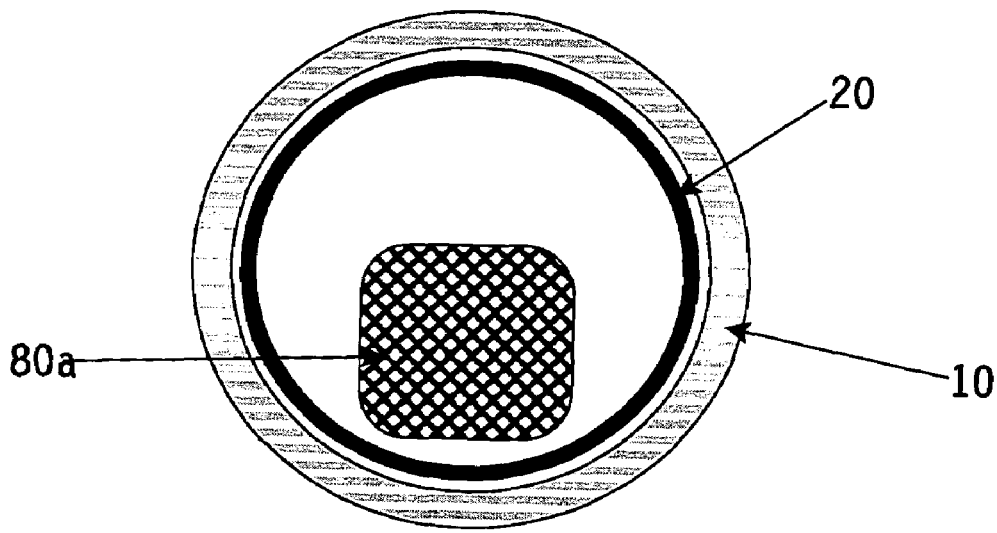
Figure 4C:
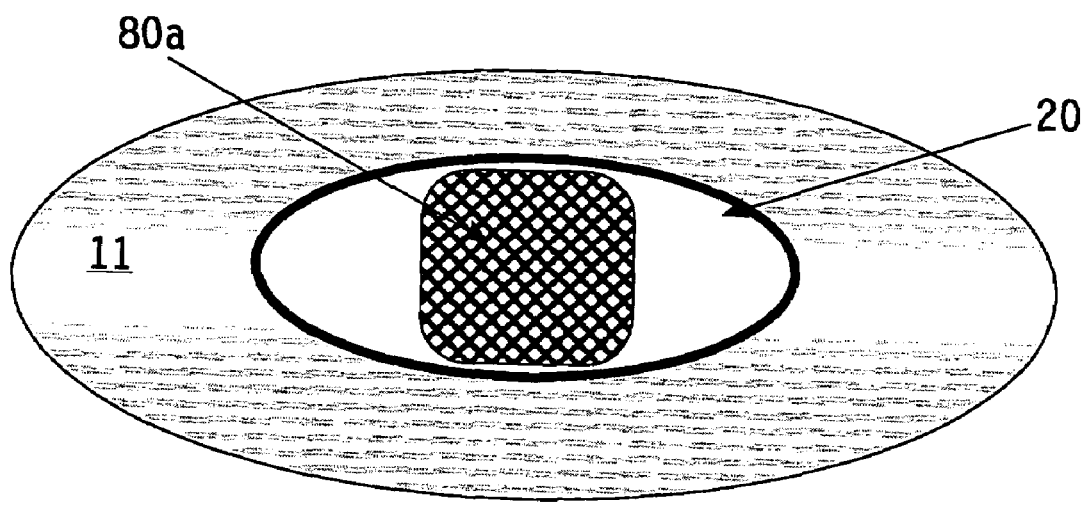

Another embodiment of the tube-shaped element 20 is disclosed in FIGS. 4a-4c wherein in FIG. 4a the tube-shaped element 20 is depicted in a state prior to the insertion through the hollow needle 10. In this embodiment the tube-shaped element 20 has an oval cross section.

When inserted through the hollow needle 10 using the tube-shaped sleeve member 30 the oval tube-shaped element 20 will follow the circular inner dimensions of the elongated hollow needle 10 and will be urged into a circular cross section as depicted in FIG. 4b.

When the hollow needle 10 is retracted together with the tube-shaped sleeve member 30 from the prostate gland 11 leaving the tube-shaped element 20 with the seed train 80a-80b at the desired radiation location within the prostate gland 11 (like FIG. 3e) the tube-shaped element 20 will return to its initial oval cross-section, as depicted in FIG. 4c. The oval shaped tube-shaped element 20 will exert an inwardly directed force on the radioactive seeds 80a and non-radioactive spacers 80b within the tube-shaped element 20 resulting in a fixation within the prostate gland 11.

This feature further limits the risk of any displacement of the seeds/spacers due to movement of the patient or other disturbances within the body (swellings, blood circulation, etc.). This phenomenon can be supported by making the tube-shaped element of a flexible or elastic material.

This same feature is also applicable to a tube-shaped element 20 with circular cross-section, wherein the outer dimensions of the seeds and spacer are equal or slightly smaller than the circular inner dimension of the element 20.

The tube-shaped element 20 thereby exerts a small friction force on the row of seeds/spacers preventing them from displacements.

It will be clear from the above that with the implanting device according to the invention a more conformal radiation treatment can be performed without the risk of irradiating fragile organs or healthy tissue as any displacement of the seeds/spacers due to movements of the patient are herewith avoided.

With reference to the FIGS. 3a-3f a method principle is disclosed, wherein the tube-shaped sleeve member 30 and the tube-shaped element 20 are mounted on the pushing rod 40, which assembly is inserted inside the hollow needle, which needle is then inserted into the animal body towards a desired location within the prostate gland 11.

With another method principle for implanting a row of radioactive seeds and non-radioactive spacers within the animal body, the hollow needle 10 is inserted into the animal body followed by the subsequent insertion of the tube-shaped element 20, the tube-shaped sleeve member 30 and the pushing rod 40.

The invention claimed is:

1. Device for implanting at least one row of X radioactive seeds and Y non-radioactive spacers with $X \in [1, 2, \ldots]$ and $Y \in [0, 1, \ldots]$ in a desired configuration to a desired location in an animal body for effecting radiation therapy of cancerous tissue in said body, said device comprising:
   a) at least one elongated hollow needle with an open distal end to be inserted towards said desired location in the body and with a proximal end to be connected to a seed loading apparatus;
   b) at least one tube-shaped sleeve member with an open distal end and an open proximal end to be slidably received within said hollow needle toward said desired location;
   c) at least one pushing element for implanting during retraction of the elongated hollow needle said row of radioactive seeds and non-radioactive spacers from said seed loading apparatus through said hollow needle and said tube-shaped sleeve member towards said location,
   d) at least one tube-shaped element with at least one open end to be inserted by said tube-shaped sleeve member through said hollow needle towards said desired location; and
   wherein
   said tube-shaped element serves to accommodate said row of radioactive seeds and non-radioactive spacers after implantation.

2. Implanting device according to claim 1, wherein said tube-shaped element is inserted through said hollow needle prior to the insertion of the row of radioactive seeds and non-radioactive spacers.

3. Implanting device according to claim 1, wherein said pushing element is constructed as a rigid pushing rod.

4. Implanting device according to claim 1, wherein said pushing element is constructed as a drive wire of the seed loading apparatus.

5. Implanting device according to claim 1, wherein said tube-shaped sleeve member is provided at its proximal end with a stopper element.

6. Implanting device according to claim 5, wherein said stopper element is constructed as a disc shaped end plate.

7. Implanting device according to claim 1, wherein the outer dimensions of the tube-shaped sleeve member and the tube-shaped element are equal or slightly smaller than the inner dimensions of said hollow needle.

8. Implanting device according to claim 1, wherein the inner dimensions of the tube-shaped sleeve and the tube-shaped element are equal or slightly larger than the outer dimensions of said radioactive seed and non-radioactive spacer.

9. Implanting device according to claim 1, wherein
$L \geq (X+Y)s$ and $S \leq (L-1)$,
in which
l is the length of the tube-shaped element;
s is the length of one individual seed/spacer;
L is the length of the hollow needle;
S is the length of the tube-shaped sleeve member.

10. Implanting device according to claim 1, wherein said tube-shaped element is made of a bio-absorbable material.

11. Implanting device according to claim 1, wherein the tube-shaped element has two open ends.

12. Implanting device according to claim 1, wherein the tube-shaped element has one closed distal end.

13. Implanting device according to claim 1, wherein prior to the insertion through the hollow needle the tube-shaped element has an oval-shaped cross section and a circular cross section when inserted in the hollow needle.

14. Implanting device according to claim 1, wherein the tube-shaped element has a circular cross section.

15. Implanting device according to claim 1, wherein the tube-shaped element is made of a flexible material for exerting an inwardly directed force on the row of radioactive seeds and non-radioactive spacers.

16. Implanting device according to claim 1, wherein at least the open end of said tube-shaped element is collapsable.

17. A seed loading apparatus provided with an implanting device according to claim 1.

18. A row of X radioactive seeds and Y non-radioactive spacers with $X \in [1, 2, \ldots]$ and $Y \in [0, 1, \ldots]$ in a desired configuration, wherein said seeds and spacers are accommodated in a tube-shaped element according to claim 1.

* * * * *